United States Patent [19]

Aburatani et al.

[11] Patent Number: 5,016,475
[45] Date of Patent: May 21, 1991

[54] WIREDRAWING APPARATUS INCLUDING AN ULTRASONIC FLAW DETECTOR

[75] Inventors: Kenji Aburatani; Tamotsu Shozaki, both of Kobe, Japan

[73] Assignee: Kabushiki Kaisha Kobe Seiko Sho, Kobe, Japan

[21] Appl. No.: 406,038

[22] Filed: Sep. 12, 1989

[51] Int. Cl.⁵ .......................................... G01N 29/00
[52] U.S. Cl. ........................................................ 73/644
[58] Field of Search .................. 73/622, 637, 638, 644

[56] References Cited

U.S. PATENT DOCUMENTS

| | | | |
|---|---|---|---|
| 3,375,706 | 4/1968 | Pandelis et al. | 73/622 |
| 3,678,735 | 7/1972 | Boulanger et al. | 73/644 |
| 4,534,405 | 8/1985 | Hulek et al. | 164/451 |

FOREIGN PATENT DOCUMENTS

| | | |
|---|---|---|
| 0080690 | of 0000 | European Pat. Off. . |
| 2311938 | of 0000 | Fed. Rep. of Germany . |
| 60-205355 | of 0000 | Japan . |
| 60250251 | of 0000 | Japan . |
| 62153744 | of 0000 | Japan . |
| 1426954 | of 0000 | United Kingdom . |
| 1585648 | of 0000 | United Kingdom . |
| 2014311 | of 0000 | United Kingdom . |
| 2137344 | of 0000 | United Kingdom . |

*Primary Examiner*—Hezron E. Williams
*Assistant Examiner*—Louis M. Arana
*Attorney, Agent, or Firm*—Oblon, Spivak, McClelland, Maier & Neustadt

[57] ABSTRACT

An ultrasonic flaw detetor for a wiredrawing apparatus, combined in a compact construction with the drawing die box and guide die box of a wiredrawing machine. The ultrasonic flaw detector comprises a cleaning tank disposed contiguously with and after the drawing box and provided with drain ports, a first partition disk having a hole for passing the drawn wire, an ultrasonic testing tank joined coaxilly to the partition disk and provided with a supply port for receiving an ultrasonic testing medium therein a second partition disk having a hole for passing the drawn wire, and a drain tank having a rear end attached to the second partition disk and a front end attached to the guide die box and provided with drain ports. The ultrasonic testing tank, the cleaning tank and the drain tank are always filled up with an ultrasonic testing medium supplied through the supply port into the ultrasonic testing tank, and the opening of the drain ports of the cleaning tank is adjusted to discharge the ultrasonic testing medium so that the cleaning tank, the ultrasonic testing tank and the drain tank are always filled up with the ultrasonic testing medium. The lubricant and the like come off the drawn wire are discharged together with the ultrasonic testing medium through the drain ports of the cleaning tank to ensure accurate ultrasonic flaw detection.

3 Claims, 3 Drawing Sheets

WIREDRAWING APPARATUS INCLUDING AN ULTRASONIC FLAW DETECTOR

BACKGROUND OF THE INVENTION

1. Field of the Invention

The present invention relates to an ultrasonic flaw detector for use in combination with a wiredrawing apparatus for drawing a linear work, such as a metal rod or wire, through a die to reduce its cross section.

2. Description of the Related Art

In a cold wiredrawing process, in general, a linear work, such as a metal rod or wire, is lubricated by a lubricant before being drawn through a drawing die. Flaws in the linear work are detected by an ultrasonic flaw detector or an eddy-current flaw detector during the cold wiredrawing process. In such a conventional wiredrawing process, the ultrasonic flaw detector is disposed, generally, between the die box and wire feeder of the wiredrawing apparatus, and an inlet guide and an outlet guide are provided, respectively, at the inlet end and outlet end of the ultrasonic flaw detector to prevent eccentricity of the linear work relative to the ultrasonic flaw detector. The ultrasonic flaw detector is provided with a normal probe and a sectional angle beam probe, which are provided within an ultrasonic testing tank, to detect mainly inclusions in the interior and under the skin of the linear work.

Such a conventional ultrasonic flaw detector for a wiredrawing apparatus requires a space for installation between the die box of the wiredrawing unit and the wire feeder and hence it is difficult to form the wiredrawing apparatus in a compact construction, flaws in the drawn wire cannot be detected because the ultrasonic flaw detector is disposed before the die box (In the following description, words for forming positional phrases, such as "before", "after", "front" and "rear", are used for denoting the sequential position of one thing relative to another with respect to the running direction of the linear work and the drawn wire.) and hence the the drawn wire drawn by a final wiredrawing process must be subjected to a separate ultrasonic testing process.

Ultrasonic flaw detection tests were performed by using the conventional ultrasonic flaw detector, in which the ultrasonic flaw detector was disposed next to the die box of a wiredrawing machine. The results of the tests showed that the lubricant applied to the linear work before wiredrawing comes off the drawn wire in flakes, the flakes of the lubricant drifted in the ultrasonic testing medium (water or oil) contained in the ultrasonic testing tank to disturb flaw detection signals, and hence accurate ultrasonic testing could not be achieved.

Although the conventional ultrasonic flaw detector having, contained in the ultrasonic testing tank, only the normal probe and the sectional angle beam probe is able to detect internal defects, such as inclusions in the interior and under the skin of the drawn wire, the conventional ultrasonic flaw detector is unable to detect chevron cracks having a substantially conical shape tapering in the drawing direction, which are internal defects occurring in drawn steel wires.

SUMMARY OF THE INVENTION

Accordingly, it is an object of the present invention to provide an ultrasonic flaw detector for use in combination with a wiredrawing apparatus, capable of being incorporated into the wiredrawing apparatus in a compact construction, capable of producing flaw detection signals of a satisfactory SNR (signal-to-noise ratio), and capable of detecting flaws in the drawn wire during the wiredrawing process.

The object of the invention is achieved by an ultrasonic flaw detector for a wiredrawing apparatus, comprising: a cleaning tank fixedly disposed downstream from the die box containing a drawing die of the wiredrawing apparatus with respect to the running direction of the linear work, and provided with a discharge port for discharging the ultrasonic testing medium; and an ultrasonic testing tank fixedly disposed next to the cleaning tank, separated from the cleaning tank by a partition wall having a hole for passing the linear work, and provided with a supply port for supplying the ultrasonic testing medium.

The ultrasonic testing tank of the ultrasonic flaw detector may be provided with a normal probe and an axial angle beam probe to detect both internal defects, such as inclusions in the interior and under the skin of the drawn wire, and chevron cracks.

The ultrasonic flaw detector can be formed in a compact construction by using the drawing die as a rear guide. Since the ultrasonic flaw detector of the present invention tests the drawn wire immediately after the drawn wire has passed the drawing die, the drawn wire produced by a final wiredrawing process need not be subjected to a separate ultrasonic testing.

The cleaning tank and the ultrasonic testing tank are separated by the partition wall having only the hole for passing the drawn wire therethrough, the ultrasonic testing tank is provided with the supply port for supplying the ultrasonic testing medium to the ultrasonic testing tank, and the cleaning tank is provided with a discharge port to discharge the ultrasonic testing medium from the cleaning tank. Therefore, the ultrasonic testing medium is supplied through the supply port into the ultrasonic testing tank at a supply rate to make the ultrasonic testing medium leak from the ultrasonic testing tank through the hole formed in the partition wall into the cleaning tank, and the ultrasonic testing medium containing the lubricant coming off the drawn wire immediately after passing the drawing die and the like is discharged through the discharge port at a discharge rate corresponding to the supply rate to prevent the flow of the lubricant and the like from the cleaning tank into the ultrasonic testing tank. Consequently, flaw detection signals of a satisfactory SNR can be obtained for accurate ultrasonic flaw detection.

The normal probe and the axial angle beam probe provided in the ultrasonic testing tank enables the simultaneous detection of both internal defects, such as inclusions in the interior and under the skin of the drawn wire, and chevron cracks.

BRIEF DESCRIPTION OF THE DRAWINGS

The above and other objects, features and advantages of the present invention will become more apparent from the following description taken in conjunction with the accompanying drawings, in which.

DETAILED DESCRIPTION OF THE PREFERRED EMBODIMENT

Figure 1:
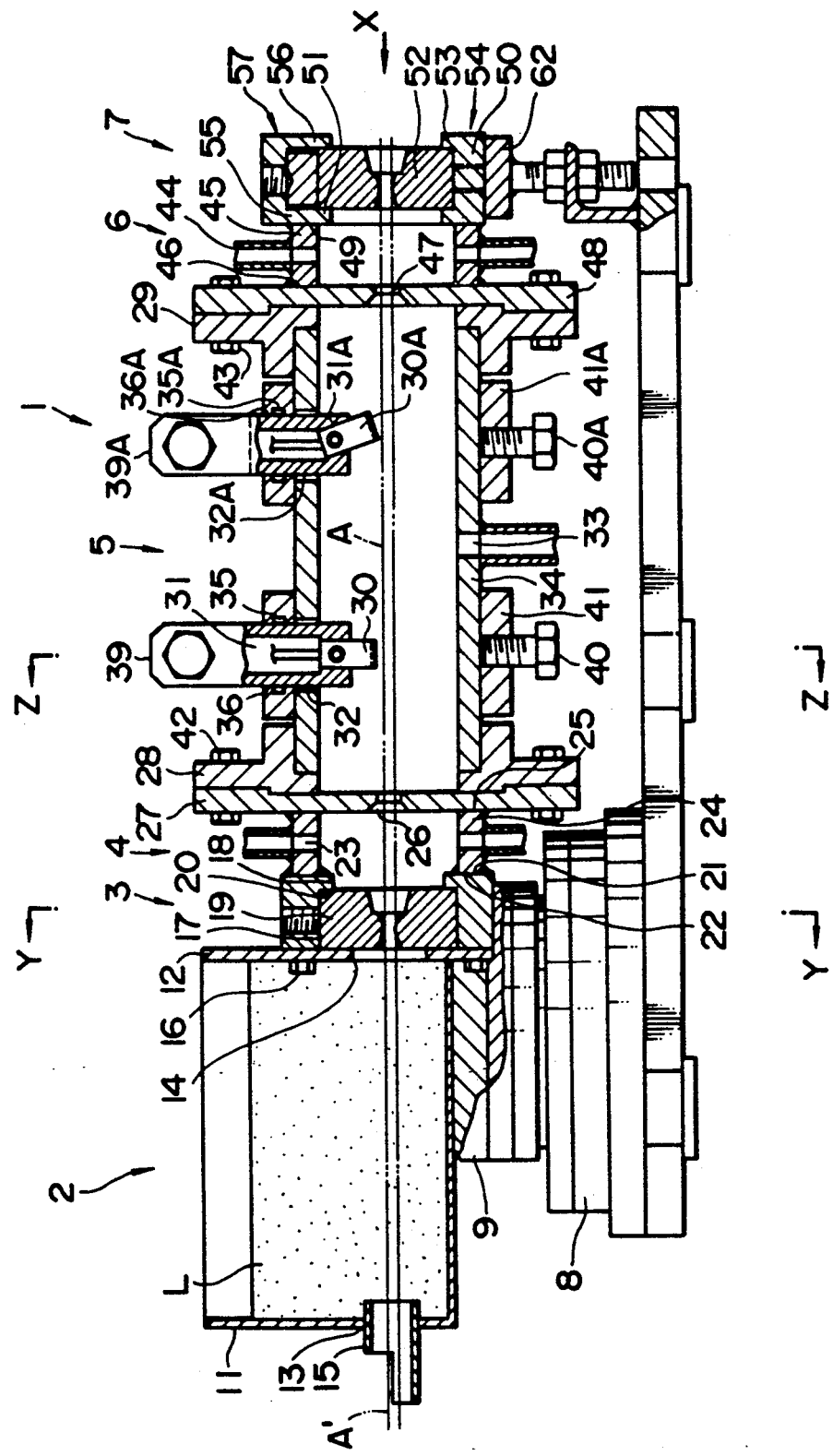
FIG. 1 is a longitudinal sectional view of an ultrasonic flaw detector in a preferred embodiment according to the present invention.
Figure 2:
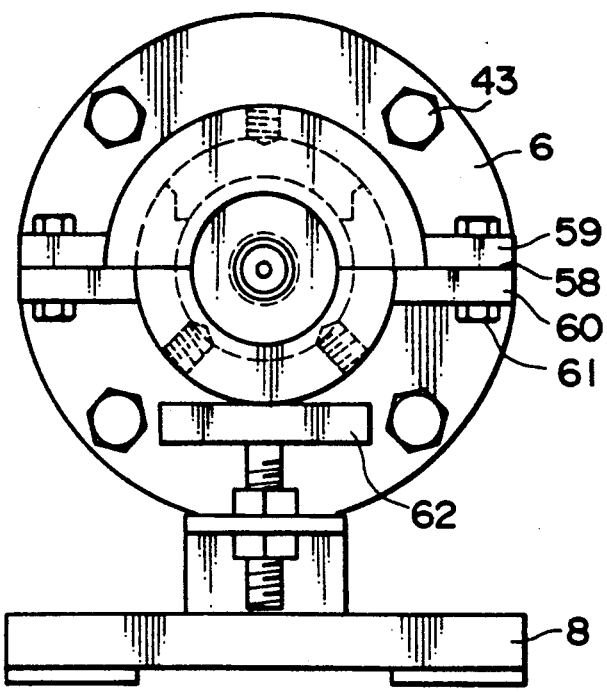
FIG. 2 is an end view of the ultrasonic flaw detector of FIG. 1; taken in the direction of an arrow X.

Referring to FIG. 1, an ultrasonic flaw detector 1 comprises a cleaning tank 4, an ultrasonic testing tank 5, and a drain tank 6 sequentially arranged in that order in the running direction of a linear work A' and fixedly joined to each other with bolts or by welding. A lubricating box 2 is disposed before and joined to a drawing die box 3 supported on a die stand 8. The cleaning tank 4 is disposed after and joined to the drawing die box 3. The drain tank is disposed before and joined to a guide die box 7 supported on and at the front end of the die stand 8.

The lubricating box 2 is formed of thin steel plates. Holes 13 and 14 are formed in the lower portions of the rear end wall 11 and the front end wall 12, respectively, to pass the linear work A' therethrough. A guide tube 15 is fitted in the hole 13 of the rear end wall 11. The front end wall 12 is fastened detachably to the rear end surface of the drawing die box 3 with bolts 16.

Figure 3:
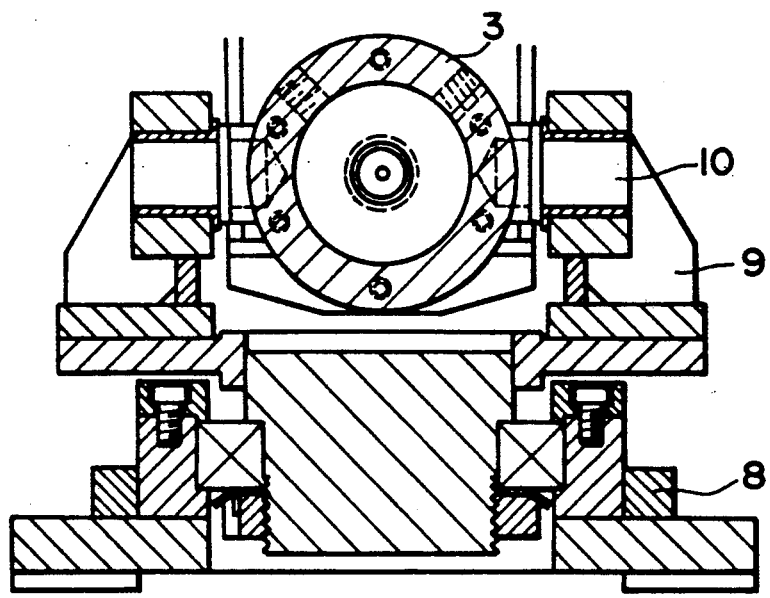
FIG. 3 is a sectional view taken on line Y—Y in FIG. 1.

The drawing die box 3 is supported pivotally for vertical swing motion by pins 10 supported on brackets 9 mounted on a die stand 8 as shown in FIG. 3. The drawing die box 3 has a shape substantially resembling a circular cylinder. A die chamber 20 is formed in the interior 17 of the drawing die box 3. A drawing die 19 is fitted in the die chamber 20 so as to be seated on the inner surface of an inner flange 18 formed at the front end of the drawing die box 3. The front end surface 21 of the drawing die box 3 is welded to the rear end surface 22 of the cleaning tank 4.

The cleaning tank 4 consists of circular cylinder 24 provided with drain ports 23 formed in the upper and lower portions thereof, and a disk 27 having a central hole 26 for passing a drawn wire A and welded to the front end surface 25 of the circular cylinder 24.

The ultrasonic testing tank 5 comprises a tubular body 34, a flange 28 attached to the rear end of the tubular body 34, a flange 29 attached to the front end of the tubular body 34, a normal probe holder 31, an angle beam probe holder 31A, a probe 30 held on the extremity of the normal probe holder 31, an angle beam probe 30A held on the extremity of the angle beam probe holder 31A, a normal probe positioning ring 41 having parallel support lugs 39 standing upright opposite to each other to hold the normal probe holder 31, provided with a hole 36 and slidably put on the tubular body 34, and an angle beam probe positioning ring 41A having parallel support lugs 39A standing upright opposite to each other to hold the angle beam probe holder 31A, and provided with a hole 36A and slidably put on the tubular body 34.

Figure 4:
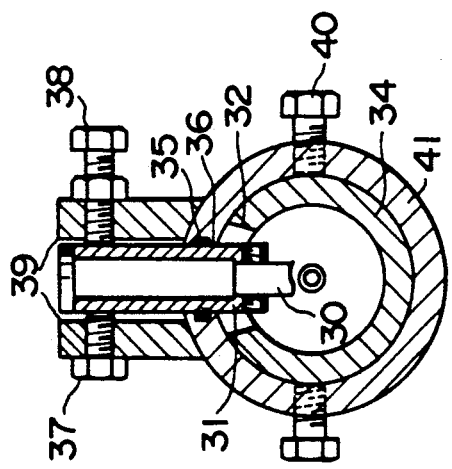
FIG. 4 is a sectional view taken on line Z—Z in FIG. 1.

Circumferentially elongate oval holes 32 and 32A are formed one after the other in upper portions of the tubular body 34 to receive the probe holders 31 and 31A therethrough, respectively, to allow the positional adjustment of the probe holders 31 and 31A in circumferential directions. A supply port 33 is formed in a lower portion of the tubular body 34 to supply water, i.e., ultrasonic testing medium, into the tubular body 34. The probe positioning rings 41 and 41A are locked at appropriate positions with bolts 40 and 40A, respectively. The normal probe holder 31 is inserted through the hole 36 of the probe positioning ring 41 and the oval hole 32 in the tubular body 34 and held on the support lugs 39 with bolts 37 and 38 as shown in FIG. 4. An O ring 35 is put in an annular groove formed in the surface of the hole 36 of the normal probe positioning ring 41 to seal the gap between the hole 36 and the normal probe holder 31. The angle beam testing probe holder 31A is inserted through the hole 36A of the probe positioning ring 41A and the oval hole 32A in the tubular body 34 and held on the support lugs 39A with bolts, not shown. An O ring 35A is put in an annular groove formed in the surface of the hole 36A of the angle beam testing probe positioning ring 41A to seal the gap between the hole 36A and the angle beam testing probe holder 31A. The flange 28 is fastened to the disk 27 of the cleaning tank 4 with bolts 42.

The drain tank 6 consists of a cylindrical body 45 provided with drain ports 44 in upper and lower portions thereof, and a disk 48 provided with a central hole 47 for passing the drawn wire A therethrough and welded to the rear end of the cylindrical body 45.

The guide die box 7 is a two-piece split box consisting of a substantially semicylindrical lower member 54 having a circular rear portion 51 welded to the front end of the cylindrical body 45 of the drain tank 6, a semicylindrical portion 50 projecting to the front from the circular rear portion 51 and provided with a semicircular inner flange 53 at the front end thereof and radial flat flanges 60, and a semicylindrical upper member 57 having a semicircular recess 55 formed in the inner surface of the rear end thereof so as to mate with the circumference of the circular rear portion 51 of the lower member 54, a semicircular inner flange 56 mating with the semicircular inner flange 53 of the lower member 54 and radial flat flanges 59 mating with the radial flat flanges 58 of the lower member 54. The lower member 54 and the upper member 57 are joined together along a joining plane 58 by fastening the radial flat flanges 59 and 60 together with bolts 61. A guide die 52 is contained in the guide die box 7 as shown in FIG. 1. As shown in FIG. 1, the guide die box 7 is supported by a height adjusting device 62 disposed at the front end of the die stand 8.

Figure 5:
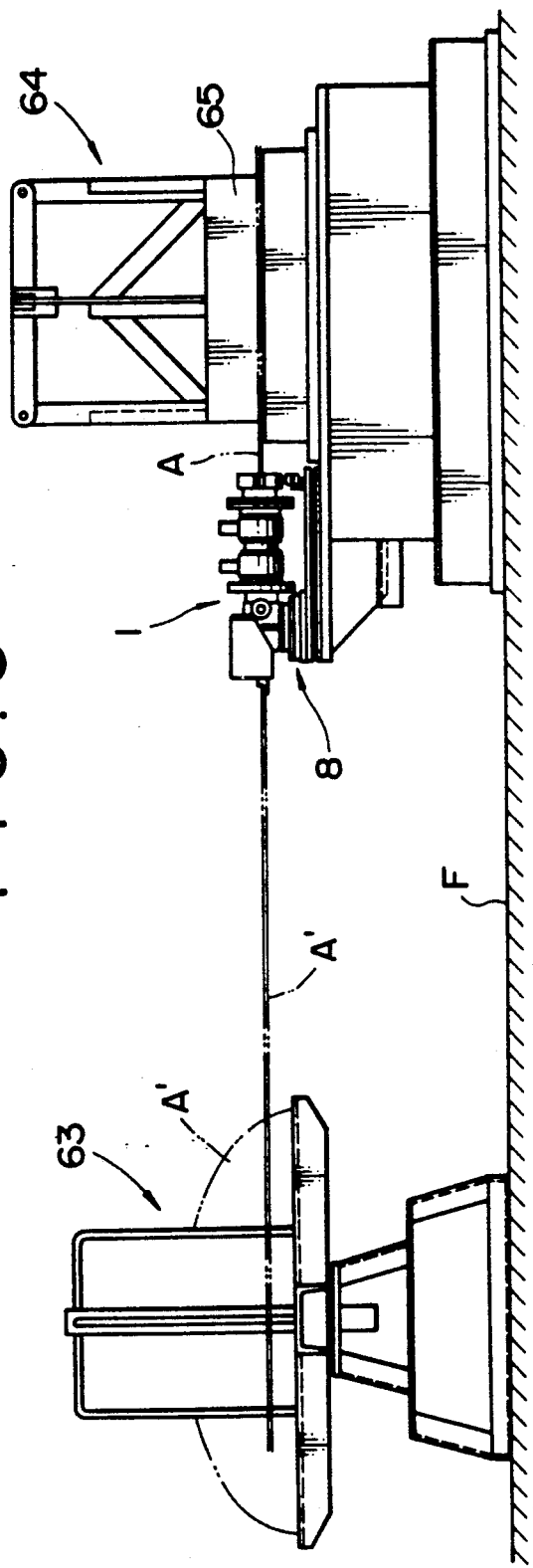
FIG. 5 is an overall view showing the operation of the invention.

The operation of the ultrasonic flaw detector 1 will be described hereinafter with reference to the drawings, particularly, FIG. 5.

The wiredrawing apparatus comprises a wire feeder 63 and a wiredrawing machine 64, which are installed fixedly on the floor F. The ultrasonic flaw detector 1 is mounted on the die stand 8 of the wiredrawing machine 64.

Prior to starting wiredrawing operation, lubricant L is put in the lubricating box 2 of the ultrasonic flaw detector 1, a drawing die 19 meeting a desired reduction ratio is put in the drawing die box 3, the normal probe holder 31 provided with the probe 30 at the extremity thereof and the angle beam probe holder 31A provided with the probe 30A at the extremity thereof are inserted through the holes 32 and 36 and through the holes 32A and 36A in the ultrasonic testing tank 5 and the holders 31 and 31A are fixed to the support lugs 39 and 39A with the bolts 37 and 38 and the bolts 37A and 38A, respectively, after positional adjustment, and a guide die 52 for drawing the drawn wire A at a reduction ratio of substantially zero is put in the guide die box 7.

Coiled linear work A' is mounted on the reel of the wire feeder 63, the leading portion of the linear work A' previously drawn to a diameter smaller than that of the guide die 52 is passed through the guide tube 15 of the lubricating box 2, the drawing die 19, the cleaning tank 4, the ultrasonic testing tank 5, the drain tank 6 and the guide die 52 and chucked by the chuck provided on the winding drum 65 of the wiredrawing machine 64. Then, the supply port 33 of the ultrasonic testing tank 5 is opened to supply water into the ultrasonic testing tank 5, the drain ports 23 of the cleaning tank 4 are opened to drain water so that the cleaning tank 4, the ultrasonic testing tank 5 and the drain tank 6 are always filled with water from the supply port 33, the drain ports 44 of the drain tank 6 are opened so that water will slightly leak from the ultrasonic testing tank 5 into the drain tank 6, and the winding drum 65 of the wiredrawing machine 64 is rotated to start wiredrawing operation.

During the wiredrawing operation, water flows constantly from the ultrasonic testing tank 5 into the cleaning tank 4 through the gap between the hole 26 of the disk 27 and the drawn wire A. Therefore, the lubricant and the like which has come off the drawn wire A after the drawn wire A has passed the drawing die 19 remains within the cleaning tank 4 and are discharged through the drain ports 23. Accordingly, the lubricant and the like which has come off the drawn wire A never flows into the ultrasonic testing tank 5 and the water heated by the drawn wire A is discharged to prevent the temperature of the water contained in the ultrasonic testing tank 5 from rising. Thus, detection signals of a satisfactory SNR can be produced for accurate ultrasonic flaw detection.

Since the water flows also from the ultrasonic testing chamber 5 into the drain tank 6 through the gap between the drawn wire A and the hole 47 of the disk 48, the water heated by the drawn wire A in the ultrasonic testing tank 5 can be immediately discharged through the drain tank 6. Thus, the rise of the temperature of the water in the ultrasonic testing tank 5 can be surely prevented to produce detection signals of a satisfactory SNR for accurate ultrasonic flaw detection.

The use of the normal probe 30 and the angle beam testing probe 30A, i.e., an axial angle beam testing probe, enables the simultaneous detection of both internal defects and chevron cracks in the drawn wire A.

The ultrasonic testing tank 5 may be constructed so as to be provided with more than two probes, including a normal probe, an axial angle beam probe and a sectional angle beam probe for more effective flaw detection.

As is apparent from the foregoing description, the ultrasonic flaw detector in accordance with the present invention for a wiredrawing apparatus has a compact construction, the drawing die box containing the drawing die, the cleaning tank and the ultrasonic testing tank arranged successively and contiguously in that order. Since the drawing die serves also as the rear guide of the ultrasonic flaw detector, the drawn wire can be subjected to ultrasonic testing immediately after passing the drawing die during the wiredrawing operation, and hence the drawn wire need not be subjected to a separate ultrasonic testing.

Although the invention has been described in its preferred form with a certain degree of particularity, obviously many changes and variations are possible therein. It is therefore to be understood that the present invention may be practiced otherwise than as specifically described herein without departing from the spirit and scope thereof.

What is claimed is:

1. A wiredrawing apparatus including an ultrasonic flaw detector, the wiredrawing apparatus having a drawing die box containing a drawing die and supported on a die stand, comprising:
   a cleaning tank disposed contiguously with and downstream from the drawing die box with respect to the running direction of a drawn wire;
   a first partition disk having a hole for passing the drawn wire and attached to the cleaning tank with the hole thereof coaxial with the drawing die;
   an ultrasonic testing tank joined to the downstream end of the first partition disk and provided with ultrasonic testing means for detecting flaws in the drawn wire and a supply port for receiving an ultrasonic testing medium therein;
   a second partition disk having a hole for passing the drawn wire and attached to the downstream end of the ultrasonic testing tank with the hole thereof coaxial with the drawing die;
   a drain tank having an upstream end attached to the second partition disk and a downstream end attached to a guide die box containing a guide die and supported at an end of the die stand, and drawing ports for draining the ultrasonic testing medium;
   wherein the hole of the first partition disk is sized sufficiently larger than the drawing die so that the ultrasonic testing medium can flow from the ultrasonic testing tank into the cleaning tank while the drawn wire is being drawn through the drawing die and the hole of the first partition disk, so as to clean the drawn wire, the cleaning tank is provided with drawing ports to discharge the ultrasonic testing medium so that the ultrasonic testing tank, the cleaning tank and the drawing tank are always filled up with the ultrasonic testing medium, and the hole of the second partition disk is formed so as to allow the ultrasonic testing medium to leak from the ultrasonic testing tank into the drain tank.

2. A wire drawing apparatus according to claim 1, wherein said ultrasonic testing tank is provided with at least a normal probe and at least an axial angle beam probe.

3. A wire drawing apparatus according to claim 1 including a lubricating box positioned upstream of the drawing die and having wire guide holes coaxial with said drawing die.

* * * * *